United States Patent
Daum

[11] 3,933,846
[45] Jan. 20, 1976

[54] PREPARATION OF BENZIMIDAZOL-2-YL-CARBAMIC ACID ALKYL ESTERS

[75] Inventor: Werner Daum, Krefeld-Bockum, Germany

[73] Assignee: Bayer Aktiengesellschaft, Leverkusen, Germany

[22] Filed: May 24, 1973

[21] Appl. No.: 363,673

[30] Foreign Application Priority Data
June 8, 1972  Germany............................ 2227919

[52] U.S. Cl............................. 260/309.2; 424/273
[51] Int. Cl.²......................................... C07D 235/32
[58] Field of Search...................... 260/309.2, 482 C

[56] References Cited
UNITED STATES PATENTS

| | | | |
|---|---|---|---|
| 2,041,733 | 5/1936 | Werntz............................ | 260/482 C |
| 2,197,479 | 4/1940 | Meigs............................. | 260/482 C |
| 3,374,265 | 3/1968 | Bossinger et al................ | 260/482 C |
| 3,649,674 | 3/1972 | Hoyer et al..................... | 260/482 C |
| 3,763,217 | 10/1973 | Brill .............................. | 260/482 C |

FOREIGN PATENTS OR APPLICATIONS

| | | | |
|---|---|---|---|
| 122,096 | 7/1901 | Germany......................... | 260/482 C |
| 544,211 | 2/1932 | Germany......................... | 260/482 C |
| 676,049 | 5/1939 | Germany......................... | 260/482 C |

*Primary Examiner*—Natalie Trousof
*Attorney, Agent, or Firm*—Burgess, Dinklage & Sprung

[57] ABSTRACT

Preparation of benzimidazol-2-yl-carbamic acid alkyl esters of the formula

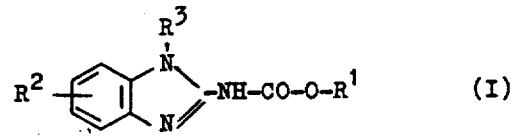

in which $R^1$ is alkyl of 1 to 12 carbon atoms optionally substituted by alkoxy, alkylmercapto, nitrile, carbamide, alkenyl, alkynyl or halogen, $R^2$ is hydrogen, halogen or lower alkyl or alkoxy, and $R^3$ is hydrogen or alkyl of 1 to 8 carbon atoms, by reacting a 2-aminobenzimidazole of the formula

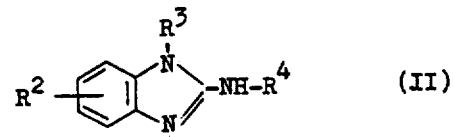

with
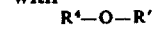

in which $R^4$ is hydrogen,

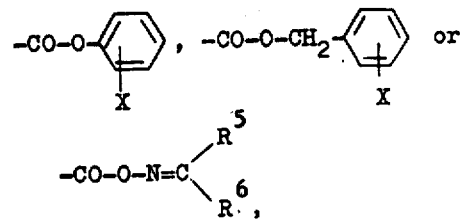

$R^5$ and $R^6$ each independently is alkyl or aryl with up to 10 carbon atoms, and X is halogen, nitro, or alkyl or alkoxy with 1 to 3 carbon atoms, provided that in formulae (II) and (III) one $R^4$ is hydrogen and the other is not.

The compounds exhibit fungicidal and mite-ovicidal activity.

10 Claims, No Drawings

PREPARATION OF BENZIMIDAZOL-2-YL-CARBAMIC ACID ALKYL ESTERS

The present invention relates to an unobvious process for the production of certain fungicidal or mite-ovicidal benzimidazol-2-yl-carbamic acid alkyl esters.

Processes for making benzimidazol-2-yl-carbamic acid alkyl esters have already been disclosed. Thus, for example U.S. Pat. No. 3,010,968 discloses reacting a S-methyl-iso-thiourea salt with 1 to 2 molar equivalents of a chlorocarbonic acid alkyl ester and then condensing this with an o-phenylenediamine, with liberation of methylmercaptan and a urethane, to give the benzimidazol-2-yl-carbamic acid alkyl ester; variants of this process have also been described in German Offenlegungsschrift (German Published Specification) No. 1,812,005. According to a further variant, Offenlegungsschrift (German Published Specification) No. 2,101,853, cyanamide is first reacted with a mercaptan to give a pseudothiourea and in a second stage the latter is reacted with chloroformic acid esters. Further methods of preparation are the reaction of chlorocarbonic acid esters with cyanamide and subsequent reaction of N-cyanourethanes with o-phenylenediamines (Belgian Patent No. 666,795) and the reaction of alkoxycarbonyl-isocyanide dichlorides with o-phenylenediamines (German Published Specification No. 1,932,297) and also reactions of allophanic acid alkyl esters or of thioallophanic acid alkyl esters with o-phenylenediamines German Offenlegungsschrift No. (Published Specification) No. 2,133,658).

The known processes mentioned have disadvantages. Thus, in designing the plant, handling of unpleasant substances such as mercaptans or hydrogen sulfide must be allowed for. The yields are often unsatisfactory. In the reaction of acid chlorides, avoiding corrosion of industrial installations represents a particular problem.

The present invention provides a process for the preparation of a benzimidazol-2-yl-carbamic acid alkyl ester of the general formula

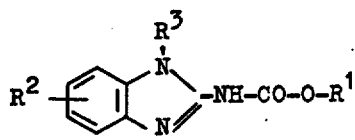 (I)

in which
$R^1$ is alkyl of 1 to 12 carbon atoms optionally substituted by alkoxy, alkylmercapto, nitrile, carbamide, alkenyl, alkynyl or halogen,
$R^2$ is hydrogen, halogen or lower alkyl or alkoxy, and
$R^3$ is hydrogen or alkyl of 1 to 8 carbon atoms, in which a 2-aminobenzimidazole of the general formula

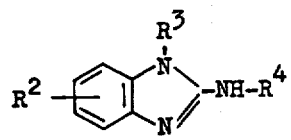 (II)

in which
$R^2$ and $R^3$ have the abovementioned meanings and $R^4$ is hydrogen,

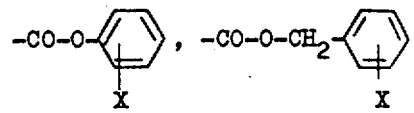

or

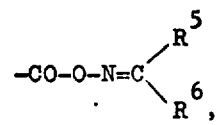

$R^5$ and $R^6$ each independently is alkyl or aryl with up to 10 carbon atoms, and
X is halogen, nitro, or alkyl or alkoxy with 1 to 3 carbon atoms,
is reacted with a compound of the general formula
$$R^4-O-R^1 \quad (III)$$
in which
$R^1$ and $R^4$ have the abovementioned meanings, provided that in formulae (II) and (III) one $R^4$ is hydrogen and the other is not.

$R^2$ preferably represents hydrogen, chlorine, methyl or methoxy. $R^3$ preferably represents hydrogen or lower alkyl with 1 to 4 carbon atoms. $R^4$ preferably represents hydrogen or phenoxycarbonyl, benyloxycarbonyl or the radical

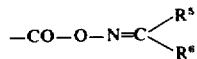

wherein $R^5$ and $R^6$ preferably represent methyl, ethyl or phenyl.

It is very surprising that the reaction of 2-amino-benzimidazoles with carbonic acid esters according to the above process represents a usable synthesis for the manufacture of benzimidazol-2-yl-carbamic acid alkyl esters, since it was to be expected that the reaction of 2-amino-benzimidazole-1-carboxylic acid esters or benzimidazol-2-yl-carbamic acid esters, once they have been formed, in the presence of as yet unreacted aminobenzimidazoles would lead to bis(benzimidazolyl)-ureas or to 2-amino-benzimidazol-1-yl-carboxylic acid benzimidazol-2-yl-amides.

The process according to the invention possesses advantages. It starts from 2-aminobenzimidazole derivatives which can easily be prepared from o-phenylenediamines. The reactions can in many cases be carried out with diphenyl-carbonate and alkanols which are inexpensive technical products. In other cases the carbonates or mixed carbonates required for the reaction can be prepared without difficulties according to known methods. Though the reactions according to the invention can also be carried out in tertiary organic bases as solvents, or tertiary bases can be used for the preparation of the starting materials, it frequently suffices, for example when preparing the particularly important benzimidazol-2-yl-carbamic acid methyl ester, to use only catalytic amounts of these expensive solvents, which particularly saves costs. The reactions can take place with very good yields and in moderately elevated temperature ranges so that the resulting heating or cooling costs are only slight. Complicated and expensive apparatus is not required for carrying out the process. The process according to the invention is new and represents a technical advance; it thus enriches the state of the art.

If 2-aminobenzimidazole and phenyl-ethyl-carbonate are used as starting substances, the course of the reaction can be represented by the following equation:

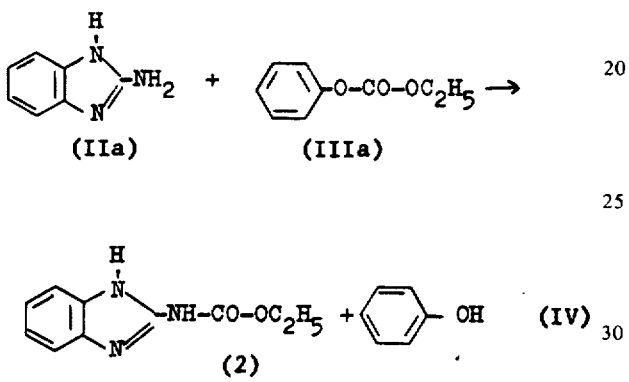

The formula (II) provides a general definition of the 2-aminobenzimidazoles or their derivatives which are to be used as starting substances. Those compounds of the formula (II) in which $R^4$ represents hydrogen are known from the literature (compare, for example, Beilstein's Handbuch der organischen Chemie (Beilstein's Handbook of Organic Chemistry), H 24, page 116); some of the compounds in which $R^4$ is not hydrogen, so that formula (II) is a N-benzimidazolyl-carbamic acid ester, are known. The last-mentioned compounds can be prepared if — as is described in detail herein — aminobenzimidazoles are reacted with carbonic acid esters in an inert solvent in the temperature range of, preferably, 50° to 100°C.

To carry out the reaction according to the invention it is possible, according to a first process variant, to react a 2-aminobenzimidazole derivative with a mixed carbonate in the presence of an inert solvent, for example benzine, toluene, xylene, dioxane, ether, acetonitrile, dimethylformamide, methylene chloride or chloroform or in a tertiary base, advantageously in the presence of a small amount of an inorganic base, such as potassium carbonate, or of an organic base, such as triethylamine or pyridine. In some cases phenols (such as phenol itself) can be used as the solvent.

The reaction temperatures can be varied over a wide range. In general, the reaction is carried out at 20 to 150°C, preferably at 50° to 100°C. If the reaction is carried out with a mixed carbonate which carries an aliphatic substituent, the benzimidazol-2-yl-carbamic acid alkyl ester is produced after some time. If, on the other hand, the reaction has been carried out with a carbonate or with a mixed carbonate which does not carry an aliphatic substituent, it is possible to isolate the benzimidazol-2-yl-carbamic acid phenyl, benzyl or ketonoxime O-esters as intermediate products and to solvolyze them, according to a second process variant, under practically the same conditions in the presence of the requisite alkanol. Advantageously, the solvolysis is carried out without isolation of these benzimidazolyl-carbamic acid esters occurring as intermediate products, after having added the alkanol to the reaction mixture. It is, however, also possible to carry out the reaction of the 2-aminobenzimidazole derivative under practically the same conditions as mentioned above with the carbonate or the mixed carbonate, merely in the presence of the alkanol. The progress of the reaction can be followed by IR-spectroscopy. If $R^3$ represents hydrogen, the corresponding 2-amino-benzimidazol-1-yl-carboxylic acid esters in some cases arise as intermediate products. Some benzimidazol-2-yl-carbamic acid alkyl esters are very sparingly soluble so that they can easily be separated off and obtained in a pure form by washing, while in other cases the reaction mixtures must be carefully concentrated and the reaction products purified by crystallization.

In accordance with one of the methods described in the last paragraph above (involving solvolysis) the invention provides a special embodiment in which a 2-aminobenzimidazole of the general formula

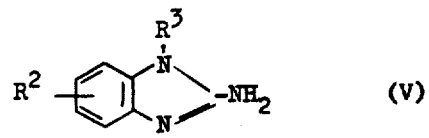

in which $R^2$ and $R^3$ have the abovementioned meanings, is reacted firstly, in the presence of a solvent, with a carbonate of the general formula

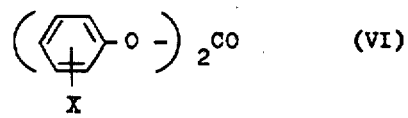

or

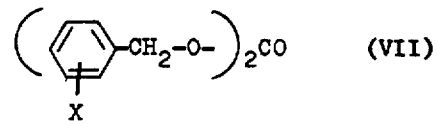

or

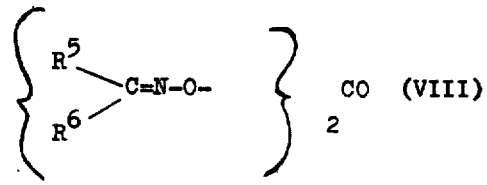

in which

X, $R^5$ and $R^6$ have the abovementioned meanings, and secondly (preferably without isolation of an intermediate product) with an alkanol of the general formula

$$HO-R^1 \qquad (IX)$$

in which $R^1$ has the abovementioned meaning.

Benzimidazol-2-yl-carbamic acid alkyl esters have aroused great interest as plant protection agents in recent years. They are used, in particular, as fungicides (compare German Offenlegungsschrift No. (German Published Specification) 1,620,175 and U.S. Pat. No. 3,657,443) and as mite ovicides (see German Offenlegungsschrift (German Published specification) No. 1,642,320 and U.S. Pat. No. 3,427,388).

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alimina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides and ovicides, or insecticides, acaricides, rodenticides, bactericides, nematocides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprises mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success i.e. by applying such compound if normally a liquid, or by applying a liquid composition containing the same, via very effective atomizing equipment, in finely divided form, e.g. average particle diameter of from 50–100 microns, or even less i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. fungi and mite ova, which comprises applying to at least one of correspondingly (a) such fungi, (b) such ova, and (f) the corresponding habitat thereof, i.e. the locus to be protected, a correspondingly combative or toxic amount, i.e. a fungicidally or ovicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating and the like.

It will be realized, of course, that the concentration of the particular active compound utilized in admixture with the carrier vehicle will depend upon the intended application. Therefore, in special cases it is possible to go above or below the aforementioned concentration ranges.

The compounds prepared according to the invention, their preparation and their use are illustrated by the following Examples.

EXAMPLE 1:

A. Preparation of the starting material:

27 g (0.203 mol) of 2-aminobenzimidazole, 43.5 g (0.203 mole) of diphenyl carbonate, 60 ml of toluene and 4 drops of pyridine were kept at a temperature of 58°C for 10 hours. The resulting benzimidazol-2-yl-carbamic acid phenyl ester was separated off and was then washed with water which contained a small amount of dodecylbenzenesulphonate. The yield was 42 g of benzimidazol-2-yl-carbamic acid phenyl ester (mentioned in British Pat. No. 1,114,069). Melting point over 330°C. IR (KBr): NH 3,380 cm$^{-1}$; NHCO 1,718 cm$^{-1}$ (m); characteristic bands at 1,640 cm$^{-1}$ (ssb), 1,605 and 1,590 cm$^{-1}$ (s), 1,202 cm$^{-1}$ and 1,050 cm$^{-1}$.

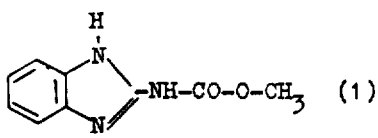

18 g (0.071 mole) of benzimidazol-2-yl-carbamic acid phenyl ester, 54 g of toluene, 54 g of methanol and 2 drops of pyridine were kept at a temperature of 67°C for 9 hours. The resulting benzimidazol-2-yl-carbamic acid methyl ester was separated off and washed with methanol and with water. The yield amounted to 12.9 g (representing 95% of theory). (The compound is known; compare U.S. Pat. No. 3,010,968.) Apart from other characteristic differences, the IR analysis in KBr showed that the NH band of the phenyl ester at 3,380 cm$^{-1}$ had disappeared and the band of the methyl ester at 3,310 cm$^{-1}$ had appeared. Phenol was isolated from the filtrate of the reaction product.

EXAMPLE 2

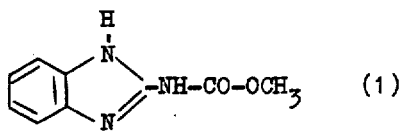

13.5 g (0.102 mole) of 2-aminobenzimidazole, 14 g (0.107 mole) of methyl-carbonic acid acetonoxime ester (known from Angew. Chemie, 69 (1957), pages 204 and 480), 50 ml of toluene and 1 drop of pyridine were kept at 50°C for 8 hours. The benzimidazol-2-yl-carbamic acid methyl ester formed was separated off and washed with toluene. Benzimidazol-2-yl-carbamic acid acetoxime ester had not been produced, as could be seen from the IR analysis (KBr), especially from the absence of the bands at 1,035 and 1,065 cm$^{-1.}$

EXAMPLE 3

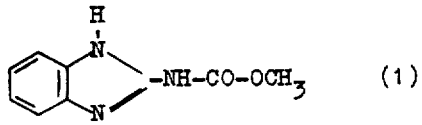

2 kg of phenol, 665.5g of 2-aminobenzimidazole, 1,180 g of diphenyl carbonate and 2 g of pyridine were kept, while being stirred, initially for 90 minutes at 60° to 68°C and then for 15 hours at 70°C. 460 g of methanol were added and the mixture further stirred for 4½ hours at 115°C in order to methanolize the carbamic acid phenyl ester. After coolong to room temperature, the benzimidazol-2-yl-carbamic acid methyl ester was filtered off, rinsed with 2.5 kg of methanol and dried at 130°C under reduced pressure. 879 g (92% of theory) of the compound of formula (1) were obtained.

EXAMPLE 4

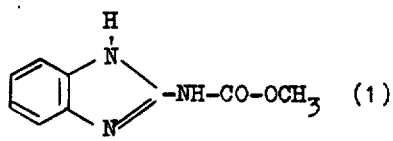

13.5 g (0.102 mole) of 2-aminobenzimidazole, 20.5 g (0.106 mole) of methyl-carbonic acid acetophenonoxime ester (prepared analogously to methyl-carbonic acid acetonoxime ester, melting point 58°-59°C) were reacted as in Example 2 15.3 g of benzimidazol-2-yl-carbamic acid methyl ester were obtained. Benzimidazol-2-yl-carbamic acid acetophenonoxime ester had not been produced, as could be seen from the IR analysis (KBr), especially from the absence of the bands at 1,045 (s) sh 1,060 cm$^{-1}$. Acetophenonoxime was isolated from the filtrate of the reaction product.

EXAMPLE 5:

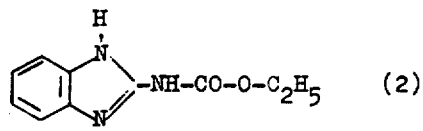

40 g (0.3 mol) of 2-aminobenzimidazole, 53 g (0.319 mol) of phenyl-ethyl-carbonate of boiling point 96°-100°C/9 mm Hg, 100 ml of toluene and 0.5 ml of picoline were kept for 1 hour at a temperature of 90°C and thereafter for 4½ hours at 110°C. The benzimidazol-2-yl-carbamic acid ethyl ester was filtered off, washed with alcohol and water and dried at 70°C. The yield was 61 g. The IR recording in KBr was identical with a sample obtained according to instructions in the literature (compare U.S. Pat. No. 3,010,968). The absence of the band at 1,050 cm$^{-1}$ showed that no benzimidazol-2-yl-carbamic acid phenyl ester had been produced. Phenol was isolated from the mother liquor of the reaction product.

EXAMPLE 6:

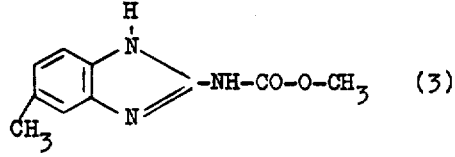

20 g of 5-methyl-benzimidazol-2-yl-carbamic acid acetoxime ester were boiled for 8 hours with 100 ml of methanol. 11.5 g of 5-methyl-benzimidazol-2-yl-carbamic acid methyl ester were obtained as a sparingly soluble precipitate. (The compound is known; compare Belgian Pat. No. 691,611.) IR spectrum (KBr): 1,092 (s) sh 1,100 cm$^{-1}$. The bands of the carbamic acid acetoxime ester were absent in the IR spectrum of the end product. Preparation of the intermediate product:

40 g (0.272 mol) of 5-methyl-2-aminobenzimidazole (known from Chem. Abstra. 40, 1595.7), 50 g of carbonic acid bis-acetonoxime ester (known from Z. Chemie 7 (1967), pages 344–5), 150 ml of xylene and 1 ml of pyridine were heated for 1 hour to 70°C and for 10 hours to 90°C. The resulting 5-methyl-benzimidazol-2-yl-carbamic acid acetoxime ester was separated off, washed with xylene and dried in vacuo. The melting point was above 300°C. IR spectrum (KBr): 920 cm$^{-1}$ (m), 1,050 cm$^{-1}$ (s).

EXAMPLE 7:

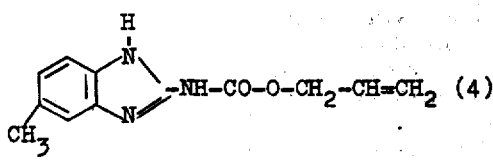

20g of 5-methyl-benzimidazol-2-yl-carbamic acid acetoxime ester and 100 ml of allyl alcohol were kept for 8 hours at a temperature of 74°C. 11.5 g of 5-methyl-benzimidazol-2-yl-carbamic acid allyl ester (known from Belgian Pat. No. 691,611) were separated off as a sparingly soluble product. The bands of the carbamic acid acetoxime ester employed were absent in the IR spectrum of the end product. IR spectrum (KBr): 1,085 (s) sh 1,095 cm$^{-1}$.

EXAMPLE 8:

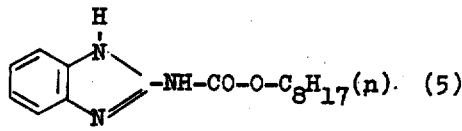

13.5 g (0.102 mol) of 2-aminobenzimidazole, 26 g of octyl-carbonic acid butanonoxime ester, 40 ml of toluene, 60 ml of xylene and 1 drop of pyridine were boiled for 8 hours under reflux and the resulting crystals (19.5 g) were separated off and washed with a little xylene. They proved to be benzimidazol-2-yl-carbamic acid octyl ester (IR spectrum (KBr): CO 1,700 cm$^{-1}$ (w); bands at 1,588 sh 1,562, 1,628 sh 1,640 cm$^{-1}$ and 1,083 cm$^{-1}$). The crystals did not contain any benzimidazol-2-yl-carbamic acid butanonoxime ester, as could be seen from the absence of the bands at 915 cm$^{-1}$, 1,040 and 1,055 cm$^{-1}$ and 1,745 cm$^{-1}$ in the IR analysis in KBr. The preparation of octyl-carbonic acid butanonoxime ester (boiling point 94°C/0.03 mm Hg) was carried out analogously to methylcarbonic acid acetoxime ester (compare Angew. Chemie. 69 (1957), pages 204 and 480).

EXAMPLE 9:

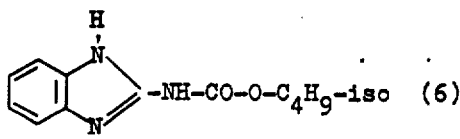

13.5 g (0.102 mol) of 2-aminobenzimidazole, 32 g (0.108 mol) of isobutylcarbonic acid 2,4,5-trichlorophenyl ester (boiling point 100°–108°C/0.3 mm Hg), 140 ml of toluene and 1 drop of pyridine were kept for 11 hours at a temperature of 58° to 80°C. The mixture was then stirred with 100 ml 5% strength sodium hydroxide solution at 0°C for 30 minutes. The organic phase was separated off, washed with water, dried over potassium carbonate and, after addition of 0.5 ml of pyridine, heated for 7 hours to a temperature of 110°C. The reaction solution was evaporated and benzimidazol-2-yl-carbamic acid isobutyl ester was recrystallised from toluene. The yield was 21 g. IR spectrum (KBr); NH 3,355 cm$^{-1}$, CO 1,704 cm$^{-1}$.

EXAMPLE 10:

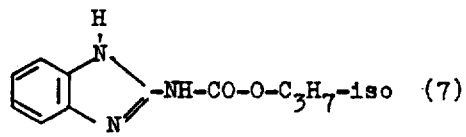

133.2 g of 2-aminobenzimidazole, 400 g of phenol, 235 g of diphenyl carbonate and 0.4 g of pyridine were stirred for 90 minutes at 60° to 68°C and 15 hours at 70°C. 150 g of isopropanol were added to the mixture which was kept at 120°C for 4½ hours. It was then cooled to 23°C and a first crystal fraction was separated off. The mother liquor was largely concentrated in vacuo. Thereafter, a second crystal fraction was isolated. Both crystal fractions were washed with isopropyl alcohol and with water and were then dried in vacuo at 120°C. Yield: 207 g of benzimidazol-2-yl-carbamic acid isopropyl ester, that is to say 94.4% of theory relative to 2-aminobenzimidazole. The IR spectrum in KBr was identical with that of a sample prepared according to U.S. Pat. No. 3,010,968.

Other compounds which may be similarly prepared include:

1-butyl-7-butoxy-benzimidazol-2-yl-carbamic acid ethoxyethyl ester, 6-bromo-benzimidazol-2-yl-carbamic acid ethylmercaptoethyl ester benzimidazol-2-yl carbamic acid ω-cyanopentyl ester, benzimidazol-2-yl-carbamic acid aminocarbonylpropyl ester, benzimidazol-2-yl-carbamic acid propargyl ester, benzimidazol-2-yl-carbamic acid 2,2,2-trifluoroethyl ester, 5-chloro-benzimidazol-2-yl-carbamic acid 2-chloroethyl ester, 4-bromo-benzimidazol-2-yl-carbamic acid 4-bromobutyl ester, and the like.

EXAMPLE 11:

Fusicladium test (apple scab) /curative
Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated additions.

Young apple seedlings in the 4–6 leaf stage were inoculated with an aqueous conidium suspension of the apple scab causative organism (*Fusicladium dendriticum* Fuckel) and incubated for 18 hours in a humidity chamber at 18°–20°C and at a relative atmospheric humidity of 100%. The plants then came into a greenhouse. They dried.

After standing for a suitable period of time, the plants were sprayed dripping wet with the spray liquid prepared in the manner described above. The plants then again came into a greenhouse.

15 days after inoculation, the infection of the apple seedlings was determined as a percentage of the untreated but also inoculated control plants.

0% means no infection; 100% means that the infection was exactly as great as in the case of the control plants.

The active compound, the concentrations of the active compound, the period of time between inoculation and spraying (dwell time) and the results obtained can be seen from the following table:

Table

| Active compound | Fusicladium test/curative Dwell time in hours | Infection in % of the untreated control at an active compound concentration (in %) of 0.025 | 0.0062 |
|---|---|---|---|
| 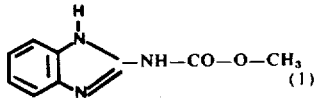 | 42 | 3 | 12 |

It will be appreciated that the instant specification and examples are set forth by way of illustration and not limitation, and that various modifications and changes may be made without departing from the spirit and scope of the present invention.

What is claimed is:

1. A process for the preparation of a benzimidazol-2-yl-carbamic acid alkyl ester of the formula

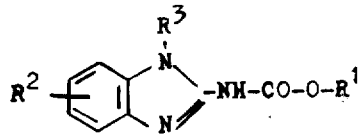

consisting essentially of reacting a 2-amino-benzimidazole of the formula

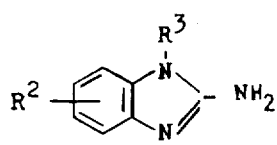

with a compound of the formula
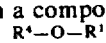  (III)
in which
R¹ is alkyl of 1 to 12 carbom atoms optionally substituted by lower alkoxy, lower alkylmercapto, lower alkenyl, lower alkynyl, nitrile, carbamide or halogen,
R² is hydrogen, halogen, lower alkyl or lower alkoxy,
R³ is hydrogen or alkyl of 1 to 8 carbon atoms,
R⁴ is $-CO-O-\underset{X}{\text{\textlangle}\bigcirc\text{\textrangle}}$ , $-CO-O-CH_2-\underset{X}{\text{\textlangle}\bigcirc\text{\textrangle}}$ or $-CO-O-N=C\underset{R^6}{\overset{R^5}{\diagup}}$ , R⁵ and R⁶ each independently is alkyl or aryl each with up to 10 carbon atoms, and
X is halogen, nitro, or alkyl or alkoxy each of 1 to 3 carbon atoms.

2. A process according to claim 1 in which the reaction is carried out in the presence of an inert solvent.

3. A process according to claim 1 in which the reaction is carried out at a temperature of about 20° to 150°C.

4. A process according to claim 2 in which the reaction is carried out at a temperature of about 50° to 100°C.

5. A process according to claim 1 wherein R² and R³ are hydrogen.

6. A process according to claim 5 wherein R¹ is methyl.

7. A process according to claim 5 wherein R¹ is ethyl.

8. A process according to claim 5 wherein R¹ is isopropyl.

9. A process for the preparation of a benzimidazol-2-yl-carbamic acid alkyl ester of the formula $R^2 \underset{N}{\overset{R^3}{\diagup}}-NH-CO-O-R^1$ consisting essentially of reacting a 2-aminobenzimidazole of the formula $R^2 \underset{N}{\overset{R^3}{\diagup}}-NH_2$ in the presence of a solvent with a carbonate of the formula $\left(\underset{X}{\text{\textlangle}\bigcirc\text{\textrangle}}-O-\right)_2 CO$ or $\left(\underset{X}{\text{\textlangle}\bigcirc\text{\textrangle}}-CH_2-O-\right)_2 CO$ or

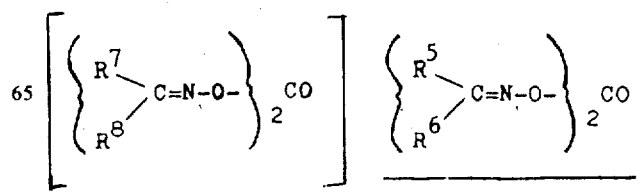

and reacting the product with a compound of the formula

H—O—R¹ in which
- R¹ is alkyl of 1 to 12 carbon atoms optionally substituted by lower alkoxy, lower alkylmercapto, lower alkenyl, lower alkynyl, nitrile, carbamide or halogen,
- R² is hydrogen, halogen, or alkyl or alkoxy each of up to 4 carbon atoms,
- R³ is hydrogen or alkyl of 1 to 8 carbon atoms,
- R⁵ and R⁶ each independently is alkyl or aryl each with up to 10 carbon atoms, and
- X is halogen, nitro, or alkyl or alkoxy each of 1 to 3 carbon atoms.

10. A process for the preparation of a benzimidazol-2-yl-carbamic acid alkyl ester of the formula

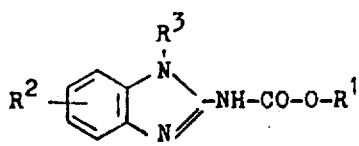

consisting essentially of reacting a 2-amino-benzimidazole of the formula

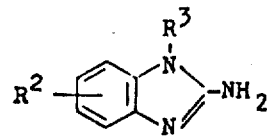

in the presence of a solvent wiht diphenyl carbonate and reacting the product with a compound of the formula

H—O—R¹ in which
- R¹ is alkyl of 1 to 12 carbon atoms,
- R² is hydrogen, halogen or alkyl or alkoxy each of up to 4 carbon atoms, and
- R³ is hydrogen or alkyl of 1 to 8 carbon atoms.

* * * * *